(12) United States Patent
Haushlater

(10) Patent No.: US 9,353,411 B2
(45) Date of Patent: May 31, 2016

(54) NUCLEIC ACID SEQUENCING TECHNIQUE USING A PH-SENSING AGENT

(75) Inventor: Robert C. Haushlater, Los Gatos, CA (US)

(73) Assignee: Parallel Synthesis Technologies, Santa Clara, CA (US)

( * ) Notice: Subject to any disclaimer, the term of this patent is extended or adjusted under 35 U.S.C. 154(b) by 1011 days.

(21) Appl. No.: 13/436,465

(22) Filed: Mar. 30, 2012

(65) Prior Publication Data

US 2013/0005583 A1    Jan. 3, 2013

Related U.S. Application Data

(60) Provisional application No. 61/469,121, filed on Mar. 30, 2011.

(51) Int. Cl.
*C12Q 1/68* (2006.01)
*G01N 21/64* (2006.01)

(52) U.S. Cl.
CPC ............ *C12Q 1/6869* (2013.01); *C12Q 1/6825* (2013.01); *G01N 21/6428* (2013.01); *C12Q 2527/119* (2013.01)

(58) Field of Classification Search
None
See application file for complete search history.

(56) References Cited

U.S. PATENT DOCUMENTS

| | | |
|---|---|---|
| 5,242,796 A | 9/1993 | Prober et al. |
| 5,750,341 A | 5/1998 | Macevicz |
| 5,969,119 A | 10/1999 | Macevicz |
| 6,210,891 B1 | 4/2001 | Nyren et al. |
| 6,831,994 B2 | 12/2004 | Bridgham et al. |
| 7,785,785 B2 | 8/2010 | Pourmand et al. |
| 2002/0155476 A1 | 10/2002 | Pourmand et al. |
| 2008/0166727 A1* | 7/2008 | Esfandyarpour et al. ......... 435/6 |
| 2008/0318244 A1* | 12/2008 | Matsunaga et al. ............... 435/6 |
| 2010/0035252 A1 | 2/2010 | Rothberg et al. |

OTHER PUBLICATIONS

Hyre et al. Cooperative hydrogen bond interactions in the streptavidin-biotin system. Protein Science 15:459-67 (2006).*
Baldock et al. Effect of acidic pH on flow cytometric detection of bacteria stained with SYBR Green I and their distinction from background. Methods Appl. Fluoresc. 1:1-9 (2013).*
John Eid, et al.; "Real-Time DNA Sequencing from Single Polymerase Molecules"; www.sciencemag.org; vol. 323, Jan. 2, 2009.
Mostafa Ronaghi, et al.; "Real-Time DNA Sequencing Using Detection of Pyrophosphate Release"; Dept. of Biochemistry, Royal Institute of Technology, S-100 44, Stockholm, Sweden; Analytical Biochemistry 242; pp. 84-89; 1996; Article No. 0432.
Jonathan M. Rothberg, et al.; "An integrated semiconductor device enabling non-optical genome sequencing"; Nature10242; doi:10.1038; vol. 475; pp. 348-352; Jul. 21, 2011; Macmillan Publishers Limited.
Jingyue Ju, et al.; "Four-color DNA sequencing by synthesis using cleavable fluorescent nucleotide reversible terminators"; www.pnas.org; Dec. 26, 2006; vol. 103, No. 52; pp. 19635-19640.
Nader Pourmand, et al.; "Direct electrical detection of DNA synthesis"; www.pnas.org; Apr. 25, 2006; vol. 103, No. 17; pp. 6466-6470.

(Continued)

*Primary Examiner* — Samuel Woolwine
(74) *Attorney, Agent, or Firm* — Kaplan Breyer Schwarz & Ottesen LLP

(57) ABSTRACT

The invention relates to a composition, method and apparatus for determining the sequence of a nucleic acid strand utilizing a pH-sensing agent.

19 Claims, 8 Drawing Sheets

Unprotonated dye molecules with surface concentration
$= x, \varepsilon_1, \lambda_{EX1}$ and $\lambda_{EM1}$.

Protonated dye molecules with surface concentration
$= x, \varepsilon_2, \lambda_{EX2}$ and $\lambda_{EM2}$.

(56) References Cited

OTHER PUBLICATIONS

Marcel Margulies, et al.; "Genome Sequencing in Open Microfabricated High Density Picoliter Reactors"; National Institute of Health (NIH); www.nature.com; Sep. 15, 2005; 437(7057), pp. 376-380.

Erik P. Anderson et al.; "A System for Multiplexed Direct Electrical Detection of DNA Synthesis"; National Institute of Health (NIH); Sens Actuators B Chem.; Jan. 29, 2008; 129(1): pp. 79-86.

* cited by examiner

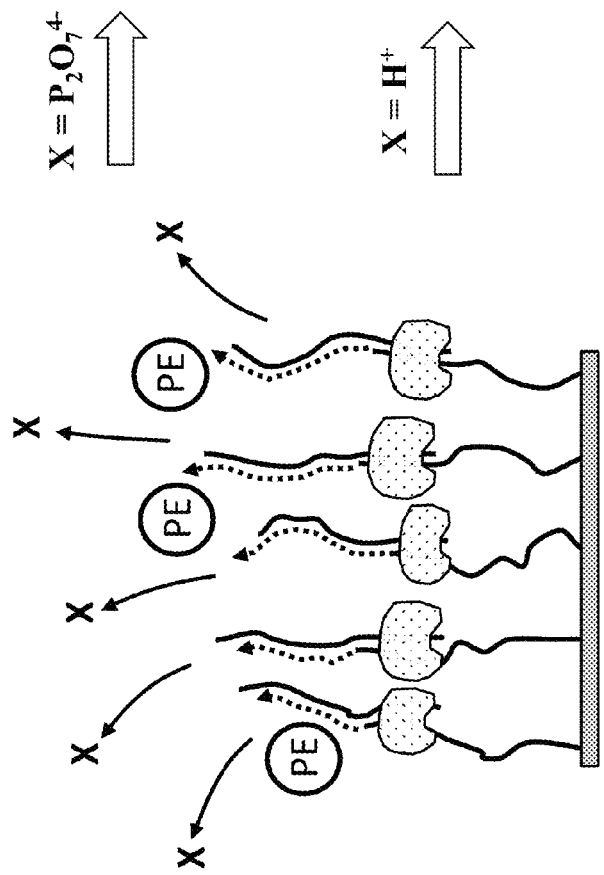

FIG. 2A

Pyrosequencing Detection: Each Primer extension cycle (i.e. incorporation of the correct dNTP) releases pyrophosphate which, through a series of coupled reactions, releases light in proportion to the dNTP incorporated $X = P_2O_7^{4-}$ Electrochemical Detection: Primer extension cycle releases a proton ($H^+$) which is electrochemically detected $X = H^+$ DyeMan Detection: Primer extension cycle releases a proton ($H^+$) which is optically detected via a pH sensitive dye $X = H^+$

NUCLEIC ACID SEQUENCING TECHNIQUE USING A PH-SENSING AGENT

FIELD OF THE INVENTION

This invention relates to techniques, methods, apparatus, reagents and materials which together form a nucleic acid sequencing system that utilizes a pH-sensing agent to sequence the order of the nucleotides in a nucleic acid strand.

BACKGROUND OF THE INVENTION

The sequencing of nucleic acids, such as deoxyribose nucleic acid ("DNA") includes determining the order of the nucleotide bases, (e.g., A, C, T and G), along a direction of a nucleic acid strand. The sequence provides detailed molecular level genetic information about the organism. Although many new sequencing technologies have been developed during recent years to sequence DNA more accurately, less expensively and faster than previous techniques, it is still a laborious, expensive and time consuming process to obtain sequencing information. For example, sequencing instruments using clonal amplification in drops or on slide colonies cost $300,000-600,000 and single molecule sequencing instruments cost above $750,000, which does not include the constant stream of very expensive chemicals, reagents and sample preparation protocols required. Much of the high cost of these sequencing systems is due to (a) the optical components (microscopes or wave guides) for systems which employ light detection, (b) the custom chip fabrication required for sequencing systems based on electrical detection and (c) the high cost of special labeled chemicals and reagents required in the single molecule-based systems. Widespread use of such valuable sequencing information is greatly hindered by these high costs. Accordingly, there is a great need to develop hardware and reagents that are vastly less expensive and allow the sequencing information to be obtained in a more efficient manner.

Several known sequencing techniques rely on primer extension (FIG. 1) to sequence the DNA. Primer extension includes a Primer (P) that is in solution or attached to the solid support, a Target (T) that contains the sequence to be determined, and a polymerase molecule. An example of one such primer extension-mediated technique, pyrosequencing, is shown in FIG. 2A In analogy to commonly used hybridization nomenclature, the DNA sequence attached to the surface is called the Probe and the species captured by hybridization is called the Target. If the capture Probe is extended by a DNA polymerase, then the Probe also functions as a Primer. In some sequencing protocols, the DNA to be sequenced is attached to the solid support and the primer to be extended is supplied from the solution. Together these components form a tripartite Probe-Target-Polymerase ("PTP") complex that can initiate primer extension. When all of the necessary auxiliary reagents are present, primer extension ensues. If the correct complementary deoxynucleotide triphosphate ("dNTP") is present, as shown in FIG. 2B, the dNTP will be incorporated into the growing primer strand (FIG. 1).

During pyrosequencing, as the PTP complex is undergoing primer extension various chemical species are released into the surrounding solution (FIG. 2A, top) including pyrophosphate ($P_2O_7^{4-}$) molecules from the cleavage of the triphosphate moiety associated with the dNTP molecules during strand incorporation. By treating the released pyrophosphate ion with a pyrophosphatase enzyme, additional chemical energy can be obtained from this hydrolysis to drive various subsequent chemical reactions. In one case, the pyrophosphate ions are coupled through various chemical species to luciferin, which emits light in proportion to the number of pyrophosphate ions released during primer extension (FIG. 2A, top). Therefore, the sequence of the target DNA strand is determined by noting how much light is released upon incorporation of the proper nucleotides.

Another example of DNA sequencing involves electrochemical detection. In this type of sequencing, when the PTP complex is undergoing primer extension protons ($H^+$) are also released. These protons may be detected using a pH meter to detect the protons released (FIG. 2A, middle and FIG. 3). While it is not difficult to detect protons electrochemically, the relatively large distance between the PTP complex and the electrodes may be up to many microns or even millimeters. This large distance between the sample and detector, as well as the diffusion and signal response rates associated with typical pH electrodes is much greater than techniques where the diffusion distances are shorter, which can lead to longer, lower analyte concentrations on the detector and more expensive analysis times.

Accordingly, there is a need in the art for a sequencing technique that utilizes a shorter diffusion distance, is easy to use, has inexpensive hardware, uses unlabeled nucleotides and inexpensive reagents and provides a more efficient high throughput screening process.

To address these limitations, disclosed herein are compositions, apparatus, and methods that include a system where the chemical sensor that detects the sequencing reaction is an integral, internal part of the surface or bead to which the nucleic acid to be sequenced is attached. As described above, all known sequencing systems have the sequencing-detecting sensor or reagents external to and physically separated from the sequencing reactions. By eliminating the optical components, external transducing sensors and highly specialized labeled reagents, a high throughput sequencing instrument may be built, using standard, commercially available components and unlabeled nucleotide reagents, that is at least 100 times less expensive than current sequencing instruments.

BRIEF SUMMARY OF THE DISCLOSURE

In one aspect of the invention, a composition for sequencing nucleic acids is provided. The composition for sequencing nucleic acids includes:
(a) a solid surface comprising a reactive group;
(b) a strand of nucleic acid
(c) a pH-sensing agent;
(d) a nucleic acid polymerase;
(e) at least one dNTP reagent; and
(f) a reaction solution.

In one aspect of the invention, a method for sequencing DNA is provided. The method for sequencing DNA includes the steps of: (A) Providing a pH-sensing agent and a reactive surface; (B) Attaching the pH-sensing agent to the reactive surface; (C) Providing a nucleic acid priming sequence; (D) Attaching the nucleic acid priming sequence to the reactive surface; (E) Providing a nucleic acid to be sequenced at least part of which is complementary to the priming sequence; (F) Providing a polymerase enzyme and a reaction solution; (G) Adding the polymerase enzyme, the reaction solution, and the nucleic acid to be sequenced to the surface containing the pH-sensitive agent and the surface-bound primer; (H) Resetting the pH-sensing agent by washing with a high pH solution; (I) Providing individual solutions of four dNTP reagents selected from: dATP, dGTP, dCTP, dTTP and combinations thereof; (J) Adding the four dNTP reagents individually and sequentially washing with the high pH solution between each addition; (K) Measuring a change in the properties of the pH-sensing agent after each addition of each dNTP; (L) Correlating the change in the properties of the pH-sensing agent with the type and amount of each dNTP added; (M) Using the change in properties to determine a nature and an amount of dNTP incorporated at each step; (N) Determining the nucleotide sequence from the dNTP incorporation data; and (O) Repeating steps (H) through (L) until the order of nucleotides in the nucleic acid strand is determined.

In one aspect of the invention, an apparatus for determining a DNA sequence is provided. The apparatus for determining a DNA sequence includes: a. light-sensitive detector covered with a high-pass interference filter or dichroic mirror; b. a surface, wherein the surface is adjacent to the light-sensitive detector and the interference filter or dichroic mirror is between the surface and the light-sensitive detector; c. an opening to introducing beads onto the surface adjacent to the detector; d. a bead dispenser or applicator to introduce beads onto the surface; e. a dispensing device to deliver reagents to the beads which contain the nucleic acid to be sequenced and to provide washing and conditioning fluids; f. an excitation source which measures the change in properties of the pH-sensitive agent; g. a low-pass excitation filter or dichroic mirror, wherein the low-pass excitation filter or dichroic mirror is located between the sample and the excitation source; and h. a means of correlating the emitted light with the amount and type of each dNTP added.

BRIEF DESCRIPTION OF THE DRAWINGS

FIG. 2A is a diagram illustrating the general scheme for pyrosequencing, electrochemical and DyeMan detection.

DETAILED DESCRIPTION OF THE INVENTION

The embodiments disclosed here comprise methods, apparatus, software functionalities and reagents that utilize a pH-sensitive agent to sequence a strand of nucleic acid. In some embodiments, this system may be referred to throughout the present application as DyeMan™ sequencing technology.

Figure 1:
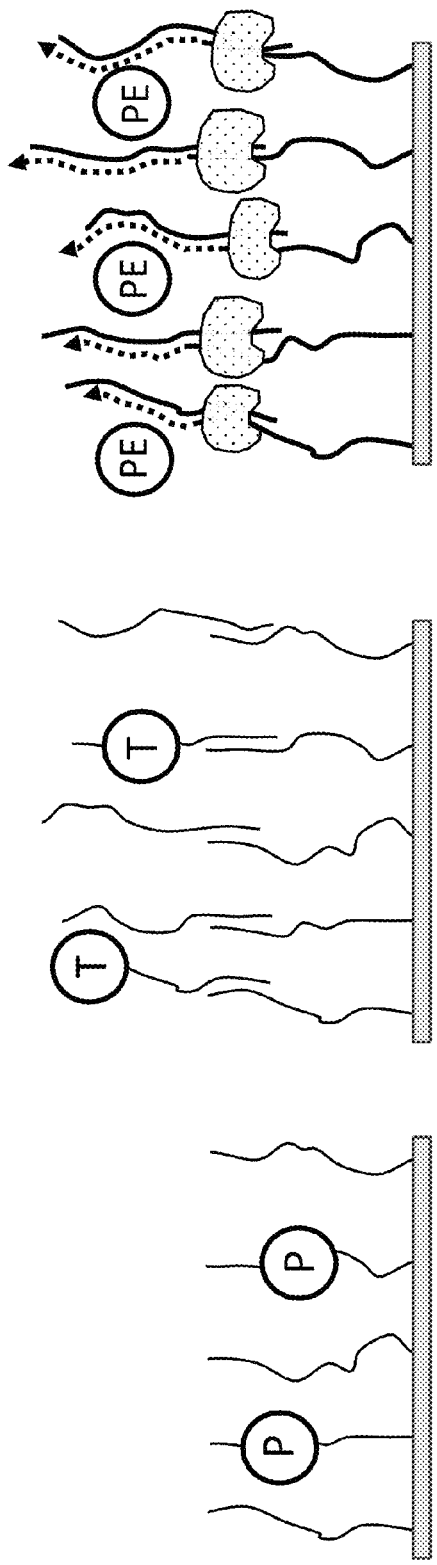
FIG. 1 is a diagram illustrating the main components of sequencing methods known in the art.
Figure 2B:
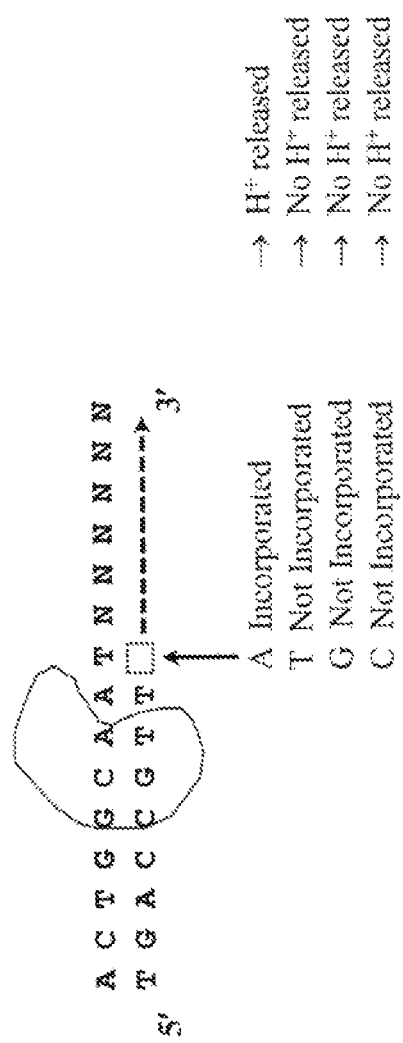
FIG. 2B is a diagram illustrating that when the correct complementary deoxynucleotide triphosphate (dNTP) is present, the dNTP will be incorporated into the growing primer strand.

As an example, which is for illustrative purposes only and should not be construed as any limitation on the scope of the invention, a primer sequence that can bind to the DNA molecule or segment to be sequenced is first attached to a bead or a region on any other solid surface (FIG. 1). After the addition of the target molecule to be sequenced, which binds to the surface-bound primer, polymerase and other reagents necessary to allow primer extension to occur are added—except for the deoxy-nucleotide triphosphate molecules (i.e. dATP, dGTP, dCTP and dTTP which are collectively referred to as dNTP). The dNTP molecules are then added sequentially one at a time and the last one removed or washed away before the next dNTP is added. When the correct dNTP is added, i.e. the dNTP corresponding to the next nucleotide (which is complementary to the corresponding nucleotide in the target strand) incorporated into the primer, which is being extended in the 5'→3' direction, a proton ($H^+$) is released (among other chemical species) with the number of protons proportional to the number of dNTP molecules incorporated (FIG. 2B). The released proton reacts with, for example, a molecule of a pH-sensing agent that is tethered to the same solid surface onto which the primer has been immobilized. The number of molecules of the pH-sensing agent protonated is proportional to the number of protons release which is in turn related to the number of the particular dNTP incorporated during that cycle of dNTP addition. Thus by measuring the change in properties of the pH-sensing agent before and after the release of the proton one can determine the type and number of dNTP molecules incorporated into the extending primer. Since this method determines sequence of the extending primer, and since the target to be sequenced is complementary to the extended primer, its sequence is therefore known.

One embodiment of the present application describes techniques, methods, apparatus, reagents and materials which together form a system for sequencing DNA by utilizing beads. This system can be used to sequence the order of the nucleotides in a molecule of DNA. In one embodiment, the technique involves detecting the protons released during primer extension from a Primer-Target-Polymerase (PTP) assembly by capture of the protons by a pH-sensing agent that results in changes in the molar absorptivity, emission efficiency, the wavelength maxima for absorption or emission of electromagnetic energy, the rate at which fluorescent emission or absorption occurs or the chemiluminescent properties of the pH-sensing agent. Examination of the optical behavior of the pH-sensing agent when the four dNTP molecules are individually added to the Probe-Target-Polymerase system provides information concerning the nucleotide sequence in the target molecule being sequenced. Since protons have a very high diffusion rate and the pH-sensing agents are in close proximity to the PTP assembly the capture of the protons is very fast and efficient, especially when there are several pH-sensing agents or more in the vicinity of the PTP assembly. In some embodiments, the pH-sensing agents may be greater than 0 nm and less than 2 nm from the PTP assembly. In some embodiments, the pH-sensing agents may be greater than 2 nm from the PTP assembly. In some embodiments it is less than 100 microns from the PTP assembly. In some embodiments the pH-sensing agent may be greater than 2 nm but less than 100 microns from the PTP assembly.

In some embodiments, the pH-sensing agent includes a dye. In some embodiments the pH-sensing agent is selected from:

| INDICATOR NAME | pH | COLOR |
|---|---|---|
| Malachite green oxalate | 2.0 | green-blue |
| Brilliant green | 2.6 | green |
| Eosin yellowish | 3.0 | green fluoresce |
| Erythrosine B | 3.6 | red |
| Methyl green | 2.3 | blue |
| Methyl violet | 2.7 | violet |
| Picric acid | 1.0 | yellow |
| Cresol red | 1.8 | yellow |
| Crystal violet | 2.6 | blue/violet |
| m-Cresol purple | 2.8 | yellow |
| Thymol blue | 2.8 | yellow |
| p-Xylenol blue | 2.8 | yellow |
| Eosin, bluish | 2.4 | pink fluoresce. |
| Quinaldine red | 3.2 | pink |
| 2,4-Dinitro phenol | 4.7 | yellow |
| 4-(Dimethylamino) azo | 4.0 | yellow/orange |
| Bromochlorophenol blue | 4.6 | blue/violet |
| Bromophenol blue | 4.6 | blue/violet |
| Congo red | 5.2 | yellow/orange |
| Methyl orange | 4.4 | yellow/orange |
| Bromocresol green | 5.4 | blue |
| 2,5-Dinitrophenol | 5.8 | yellow |
| Alizarin sulphonic acid | 6.3 | violet |
| Methyl red | 6.2 | yellow/orange |
| Chlorophenol red | 6.4 | purple |
| Litmus | 8.0 | blue |
| Bromocresol purple | 6.8 | purple |
| Bromophenol red | 6.8 | purple |
| 4-Nitrophenol | 7.5 | yellow |
| Bromoxylenol blue | 7.5 | blue |
| Bromothymol blue | 7.6 | blue |
| Phenol red | 8.2 | red/violet |
| 3-Nitrophenol | 8.6 | yellow/orange |
| Neutral red | 8.0 | orange/yellow |
| Creosol red | 8.8 | purple |
| 1-Naphtholphthalein | 8.3 | blue/green |
| m-Cresol purple | 9.0 | purple |
| Thymol blue | 9.6 | blue |
| p-Xylenol blue | 9.6 | blue |
| Phenolphthalein | 9.8 | red/violet |
| Thymolphthalein | 10.5 | blue |
| Alkali blue | 14.0 | pink |
| Alizarin yellow GG | 12.1 | brown/yellow |
| Indigo carmine | 13.0 | yellow |
| Epsilon blue | 13.0 | violet |
| Titan yellow | 13.0 | red. |

In one embodiment, the sequencing procedure is performed on a bead or other solid substrate surface where the primer and pH-sensing agent are both bonded to the surface in close proximity on a molecular length scale. The close association of the PTP complexes emitting the protons and pH-sensing agent, in some cases with less than 1 nm separation, results in efficient and very rapid capture of the proton by the dye pH-sensing agent. In contrast, methods in which the released protons are detected with a pH-sensing electrode are (a) much slower to detect the event because the protons have to diffuse over much larger distances (nm versus μm) and (b) less sensitive because the protons diffuse from the beads in all directions before reaching the sensing electrode whereas the protons in the of the pH-sensing agent are all captured by the proximate pH-sensing agent before they can diffuse from the bead or surface thereby improving both the speed and lower limits of detection.

In some embodiments, the pH-sensing agent is a pH-sensing dye. In one exemplary instance, the pH-sensing dye is colorless throughout the visible spectrum region at a pH of 8-9. The same dye becomes fluorescent when the PTP complex releases a proton upon primer extension and the dye responds to higher pH. The fact that this type of dye is colorless at a pH of approximately 8-9 and is fluorescent at a pH of approximately 4-5, is particularly advantageous for detection because (a) the fluorescent light is emitted against a dark background and (b) when the bead is "reset" back to its colorless state after $H^+$ detection using the pH=8-9 buffer it provides an individual negative background control for each bead.

It is abundantly clear to those skilled in the art that there are various combinations and concentrations of other pH sensitive dyes, dyes with other optical properties (including absorbance, emission and excitation properties), buffers with different pH values, polymerase molecules, capture probes and primers that can be combined to perform related sequencing reactions.

In order to detect changes related to the sequence determination, the surfaces on which the sequencing may be imaged with conventional optical apparatus, such as a microscope with appropriate light sources, excitation filters and emission filters, or in a far less expensive manner by placing the beads directly onto the surface of a pixelated detector, such as a complementary metal oxide semiconductor (CMOS) or a charge coupled device (CCD). By including a thin film interference filter or appropriate dichroic mirror between the beads and the detector the fluorescent emission from each bead may be measured upon appropriate excitation.

It is clear to those skilled in the art that many other permutations and variations of this technology exist, such as dyes with various absorption and emission properties, different reagent and polymerase mixtures, different surfaces or beads and whether some or all of the reagents are tethered to the surface of the solid substrate, all of which represent improvements over the current schemes for sequencing DNA.

Sequencing Methods Related to Primer Extension

As mentioned above, several techniques rely on primer extension to sequence DNA. As shown in FIG. 1 there is a primer (P) which is attached to the solid support, a target T (which contains the sequence to be determined) and a polymerase molecule which together form the tripartite Probe-Target-Polymerase (PTP) complex which can initiate primer extension when placed in the reaction solution. When all of the necessary auxiliary reagents are present primer extension is initiated and, if the correct complementary dNTP is present (FIG. 2B), the dNTP will be incorporating into the growing primer strand (FIG. 1).

As the PTP complex is undergoing primer extension various chemical species are released into the surrounding solution (FIG. 2) including pyrophosphate ($P_2O_7^{4-}$) molecules from the cleavage of the triphosphate moiety associated with the dNTP molecules during strand incorporation. By treating the released pyrophosphate ion with a pyrophosphatase enzyme, additional chemical energy can be obtained from this hydrolysis to drive various subsequent chemical reactions. In one case, the pyrophosphate ions are coupled through various chemical species to luciferin, which emits light in proportion to the number of pyrophosphate ions released during primer extension (FIG. 2A top). Therefore, the sequence of the target DNA strand is determined by noting how much light is released upon incorporation of the proper nucleotides. The emitted light is detected by a light-sensitive detector, such as a CMOS photosensor, CCD or imaging plate, external to the sequencing reaction.

Figure 3:
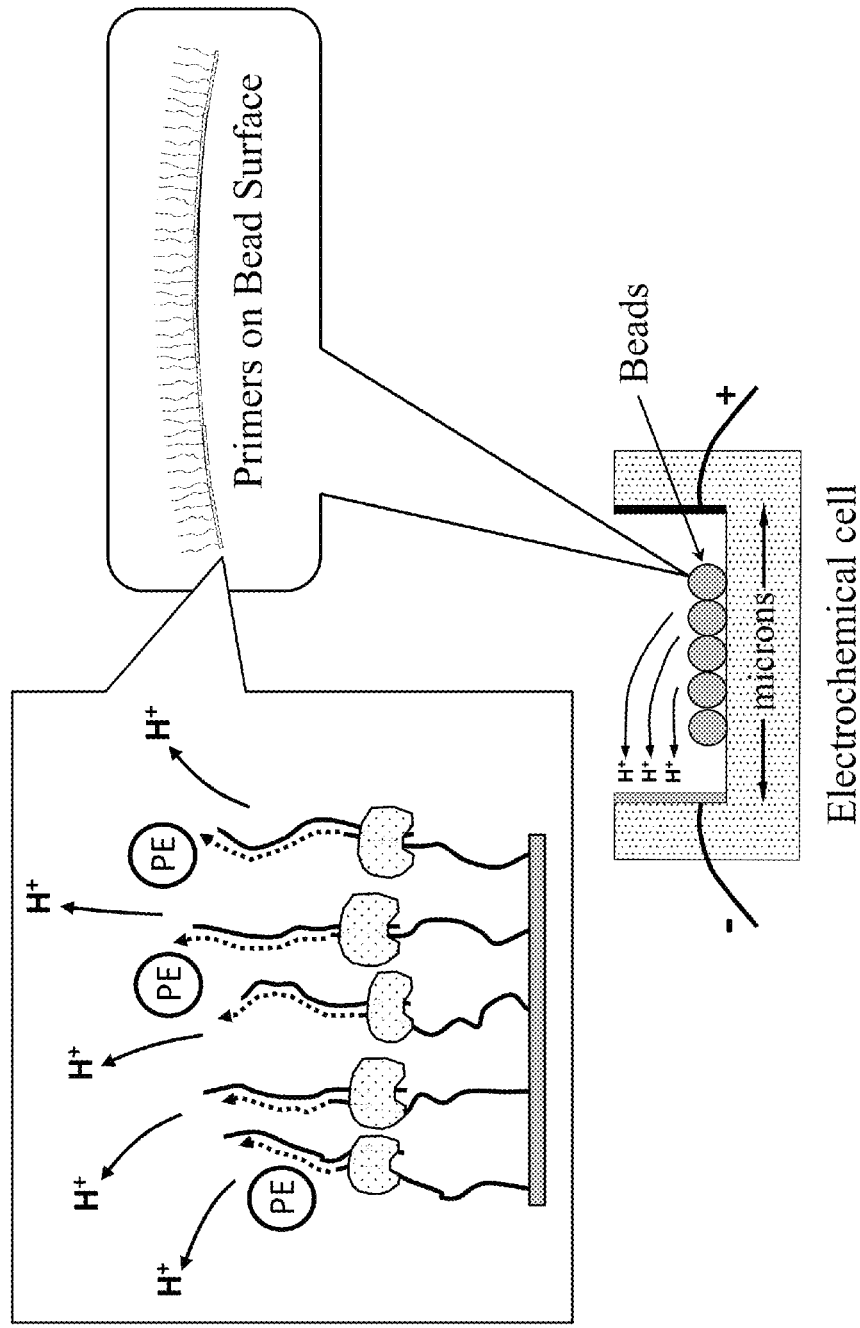
FIG. 3 is a diagram illustrating electrochemical detection of protons released during primer extension.

When the PTP complex is undergoing primer extension protons ($H^+$) are also released. These protons may be detected using a pH meter to detect the protons released (FIG. 2A middle and FIG. 3). While it is not difficult to detect protons electrochemically, the relatively large distance between the PTP complex and the external electrodes may be up to many microns or even millimeters. This large distance between the sample and detector, as well as the diffusion and signal response rates associated with typical pH electrodes is much greater than techniques where the diffusion distances are shorter, which can lead to longer and more expensive analysis times.

Figure 4:
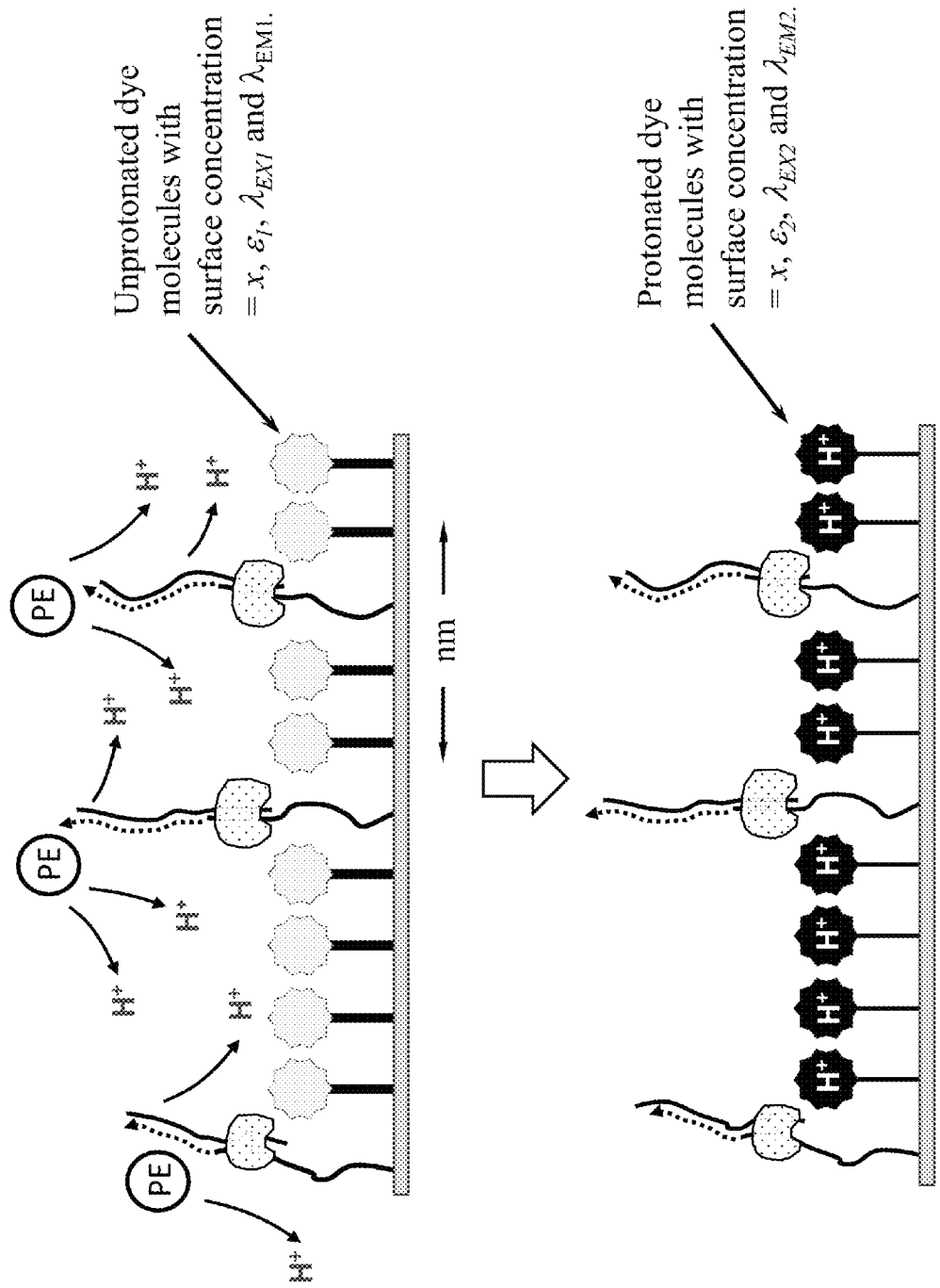
FIG. 4 is a diagram illustrating that when a primer is extended the protons released can change the optical properties of a pH-sensing reagent.

In contrast to the techniques utilized in the prior art, the "sensor" for the present invention is not a distant mechanical or chip-based device that is many molecular diameters (up to microns) away from the PTP complex but rather, in one exemplary embodiment, a pH-sensing agent (e.g., a pH-sensing dye molecule whose optical or physical properties change with pH) which could be under 1 nm away in distance. When the protons are released from the PTP complex the nearby pH-sensing dye or other species undergo a change in their optical or other physical properties, which may be correlated with the type and number of nucleotides incorporated into the extending primer, i.e. determining the sequence of the nucleotide sequence in the target DNA strand being sequenced. For example, the change in optical property could be the dye changing its absorption wavelength (from $\lambda_{EXC1}$ to $\lambda_{EXC2}$), its emission wavelength (from $\lambda_{EM1}$ to $\lambda_{EM2}$), its surface concentration (x) relative to the surface concentration of the PTP complex (y), its molar absorptivity ($\epsilon$) or emission quantum yield (FIG. 4).

Figure 7:
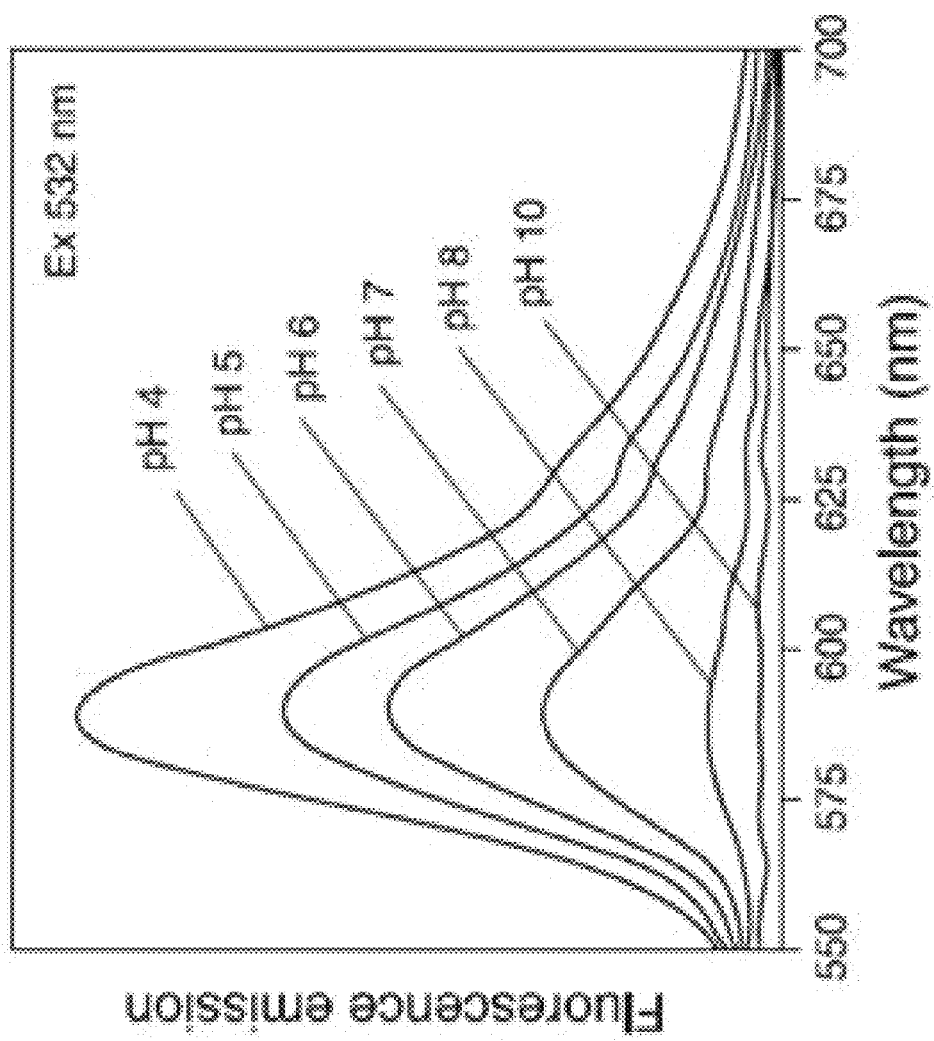
FIG. 7 is a graph that plots fluorescent emission intensity versus pH utilizing pHrodo dye in accordance with the present invention. An example of a dye (pHrodo dye from Invitrogen) that is fluorescent at lower pH (pH=4) but not fluorescent at higher pH (pH=10).

In one advantageous embodiment, the dye is a fluorescent dye that is only fluorescent when it is in the protonated form (dye H$^+$) but not fluorescent in its unprotonated state. This configuration is particularly advantageous because (a) the fluorescent signal is obtained against a dark background of the unprotonated species and (b) each particle provides its own negative control at the beginning of each dNTP addition cycle by resetting the dye to its colorless, non-fluorescent state. An example of a dye of this type is the pHrodo™ pH-sensing dye from Invitrogen (FIG. 7). It is more than abundantly obvious to those skilled in the art that there are many other chemical or physical properties for the dye sensors which could undergo a detectable change upon reaction with a proton or proton-generated species such as a change in color, change in absorptivity or emission wavelengths. For example, the protonated dye could be fluorescent and the protonated form less fluorescent or the protonated form absorbs light of some wavelength while the unprotonated form absorbs more or less of that same wavelength than the protonated form. Likewise, the released proton could trigger a series of coupled reactions where the initially protonated species further reacts with a secondary species which is the species ultimately detected as is the case with the Pyrosequencing reactions discussed above. In addition to changes in the pH-sensing agent's optical properties, the released protons could also induce geometric changes or isomerization in the pH-sensing agent, which may be detected by optical, vibrational or other types of spectroscopic methods.

Furthermore, it is clear that the electrochemical detection geometry shown in FIG. 3 allows some substantial portion of the released protons to diffuse away into the bulk solution and remain undetected. In contrast, when the extending primers are surrounded by pH-sensing agents in close proximity there is a greater chance of capturing the protons before they diffuse into the bulk thereby increasing not only the detection speed but the efficiency of the proton-detecting reaction which in turn provides lower detection limits.

It is clear that it would be possible to perform the sequencing techniques of the present invention by designing a chemiluminescent molecule, either attached to the surface or free floating in solution, which spontaneously emits light upon protonation resulting from primer extension.

In the sequencing technique of the present invention, the proton sensing reaction takes place very rapidly due to the very short diffusion distances which are comparable to one molecular diameter. In one advantageous exemplary embodiment both the PTP complex and the pH-sensing agent molecules are bonded in a comingled fashion onto the surface of a bead or a porous bead with a high surface area and large pores capable of binding sufficient material for facile detection such that when the proton is released it immediately reacts with a proximate unprotonated dye molecule. As compared to substrates containing microfabricated pH meters on a solid substrate, a single bead can be much smaller than a pH sensor and its associated circuitry, which means the mixing and diffusion rates will be even faster resulting in a more rapid analysis.

It should also be clear to those skilled in the art that in other embodiments it may be possible to perform the sequencing technique of the present invention with the dye free-floating within the pores of the bead rather than attached to the surface.

In one advantageous embodiment is where the pK of the dye is pK≥7 so that the protons readily react with the dye molecules. Furthermore, if there are an excess of dye molecules with a pK≥7, then (a) the pH of the solution will be buffered at the pK of the dye (b) the dye molecules will favor capture of all protons because of the large molar excess of pK≥7 dye.

In some embodiments, the sequencing technique includes a reaction solution. In some embodiments, the reaction solution includes a PCR mix. The PCR mix may be any PCR mix known in the art. For example the PCR mix may include any reaction materials such as individual nucleotides or dNTP molecules, primers, polymerase enzymes, reagents, magnesium ions, polyethylene glycol, cofactors, or any other materials known in the art and combinations thereof.

Other embodiments disclosed here for configuring the surface type and concentration of the molecules required for sequencing include:
 (a) Attaching the pH-sensing agent by a covalent bond, with or without intervening linker molecules to control the distance from the surface and the local chemical environments on the reaction surface;
 (b) Attaching the pH-sensing agent by first covalently bonding the pH-sensing agent to a DNA oligonucleotide and then hybridizing this dye-DNA moiety to a complementary strand of DNA anchored previously to the solid surface;
 (c) Controlling the relative ratios of all sequencing reagents and pH-sensing agent on the surface or in solution above the surface; and
 (d) Increasing the concentration of the polymerase, and all other reagents, by attaching the Probe, pH-sensing agent and polymerase to the solid surface by direct covalent attachment, electrostatic attachment, hydrogen bonding or via complementary DNA strands on the surface and species to be immobilized onto the surface.

Optical Methods for Sensing Primer Extension

This section provides descriptions of methods and apparatus to optically detect the release of a proton during primer extension of the PTP complex. One method, which is used as an example only, involves measuring the change in fluorescence of a pH-sensing dye molecule that is in close proximity to the PTP complex from which the protons emanate. There are many methods by which the fluorescence or other optical or physical properties of the substrate surface may be measured. A typical and well known method to those skilled in the art to measure fluorescence from a surface or bead would include the use of a microscope, which would have sufficient resolution to acquire statistically meaningful data, to acquire image data on the surface or beads. The apparatus involves an excitation source, an excitation optical filter, a sample whose optical, chemical or physical properties are being measured, an emission optical filter and an optical detector. Often an image of the beads or surface is obtained that is analyzed for such properties as color, brightness and amount present. Using this apparatus, fluorescence, emission or chemiluminescent from the surface or bead can be measured and the sequence of the DNA determined by associating the change in optical properties with successful primer extension as discussed above.

Microscopes and optical components are generally very expensive. Accordingly, it would be very advantageous to one of skill in the art to be able to detect the light output of the beads or surface without a microscope or expensive optical components.

Figure 5:
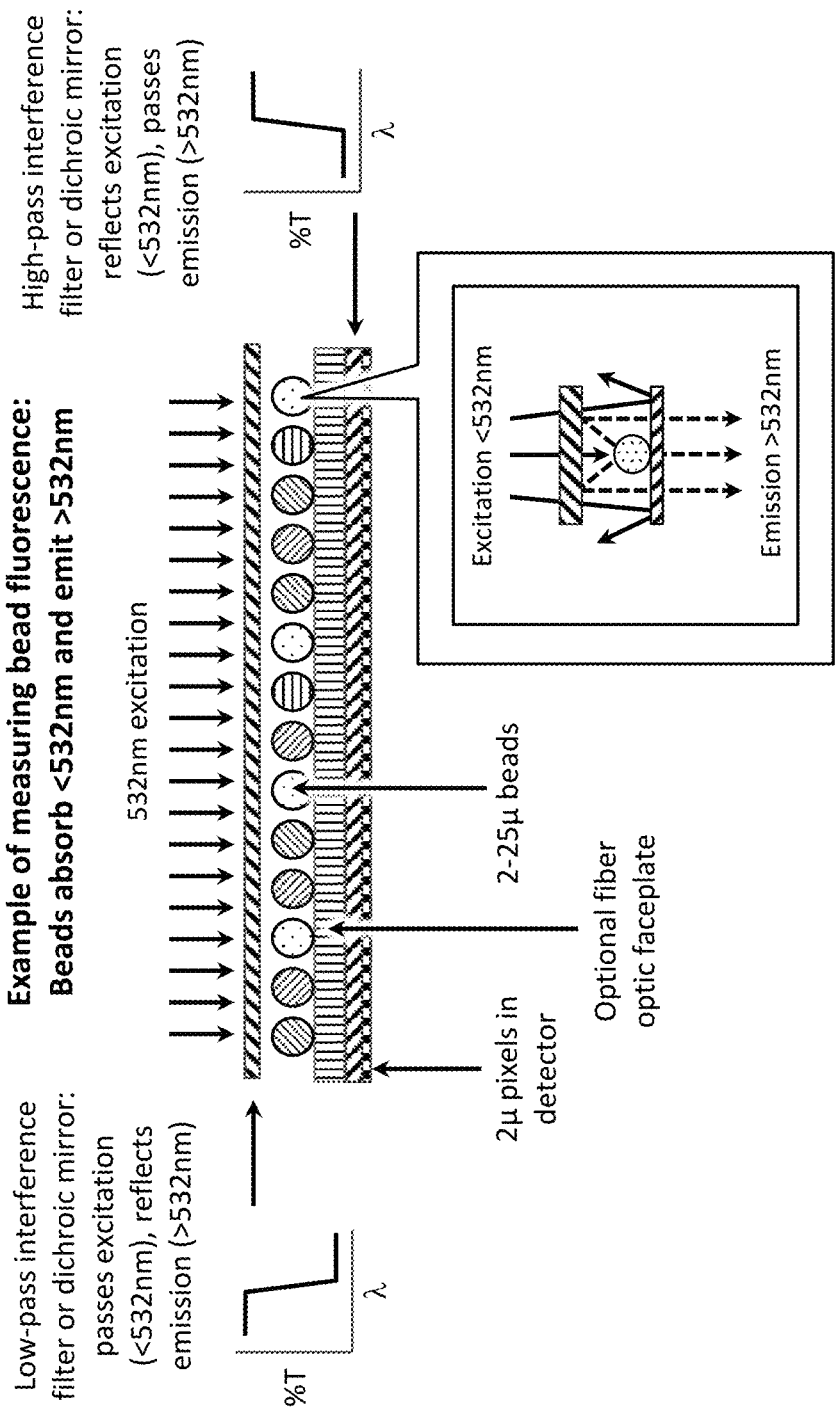
FIG. 5 is a diagram illustrating an apparatus for reading the optical signals from a sequencing system according to the present invention.

An alternative method, which is for illustrative purposes only and should not be construed as limiting the scope of the invention in any way, involves the use of the sample, sensor and filter configuration shown in FIG. 5. The apparatus in FIG. 5 measures the emitted light of an effulgent species, fluorescence, phosphorescence or chemiluminescence. It is easy to understand that the absorption, rather than the emission, of light could likewise be employed to accomplish similar determinations.

Figure 6:
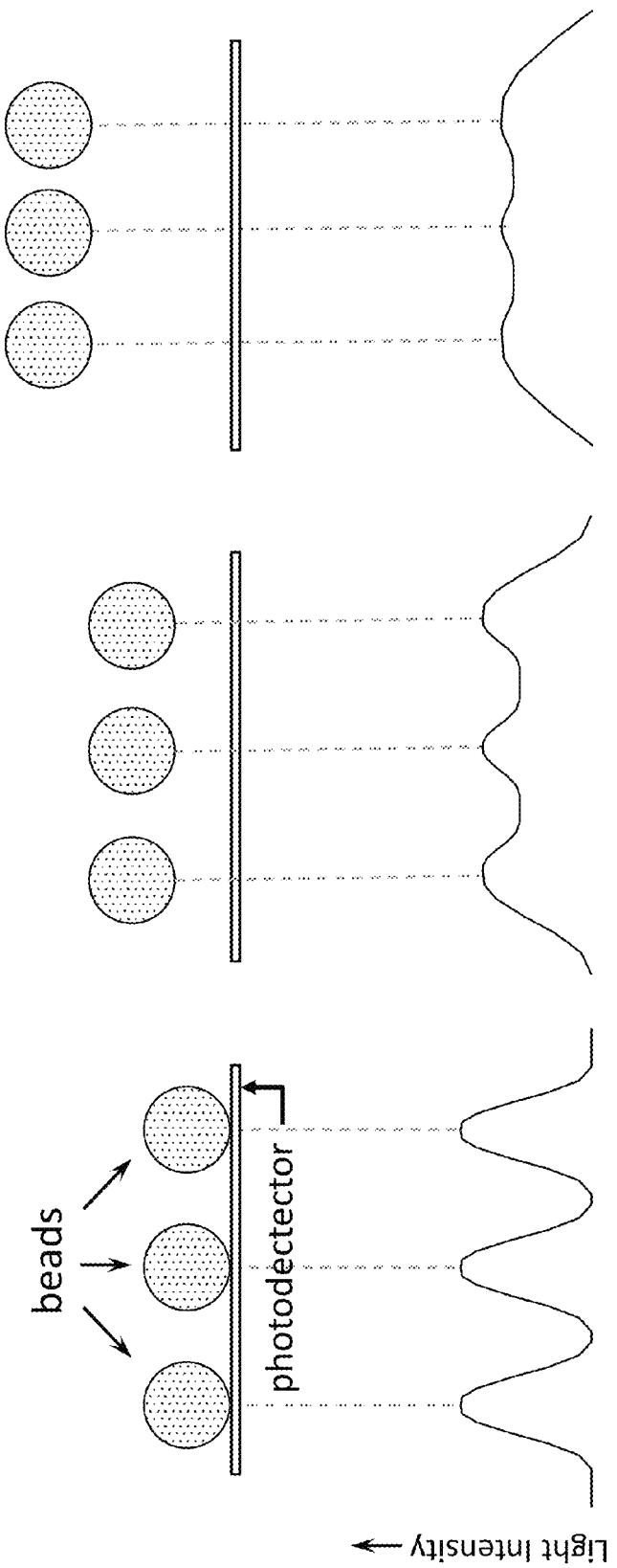
FIG. 6 is a diagram illustrating the position of x on a detector verse light intensity. The amount of light emanating from beads can be determined without creating a typical image with expensive optical components such as microscope objectives that create an image on the focal plane of a detector if the beads are not smaller than the pixels in the detector. In this case, the light is detected by a CMOS photosensor, a CCD detector, photographic film or any other light-sensitive device which can measure the brightness of a light source. As shown in the left part of the FIG. 6, when the distance of the beads to the surface is smaller than the diameter of the bead the light emitted from a given bead can be associated with a single bead with little interference or overlap from the light emitted from proximate beads. As the distance from the beads to the detector increases it becomes increasingly difficult to associate the light on the detector with a given beads.

It is important in this apparatus to place the beads as close as possible to the detector surface in order to prevent optical cross talk between proximate beads or nearby adjacent regions on a solid surface. When the beads or surface feature are sufficiently close to the surface of the sensor, the light emitted directly under a given bead may be unambiguously assigned to that bead but as the distance between the detector and surface or bead increases the light emitted from an individual bead spreads out on the detector becoming less intense and begins to merge with the light emitted by adjacent beads or surface features. This is illustrated schematically in FIG. 6.

The apparatus (FIG. 5), which is only one of many possible configurations comprising a bead or surface detector and should not be considered to limit the scope of any inventions disclosed here, functions as follows:

(a) A CCD, CMOS or other light-sensitive detector is covered with a thin high-pass interference filter (i.e., a so-called emission filter) or suitable dichroic mirror which passes the emitted light from the sample but blocks the excitation wavelengths impinging on the sample; the pixels of the detector should be comparable in size or smaller than the object to be measured for the best imaging statistics;

(b) An optional linear or tapered fiber optic face plate (bundled fiber array to transfer an image from one face of the plate or taper to the other) is placed onto the sensor; a tapered fiber bundle could provide magnification or diminution of the image on opposite faces of the taper depending on its orientation;

(c) The beads or surfaces to be measured are placed in direct contact with the detector or optional fiber face plate, or as closely as possible, in a manner which will allow the solutions of the dNTP and other necessary reagents to be flowed over, by and through the bead or surface samples on or near the detector;

(d) A low-pass excitation filter or suitable dichroic mirror, which passes the excitation wavelengths but blocks or reflects the emitted light from the sample, is placed between the sample and the excitation source; the excitation source may be any luminous source such as an LED, a filament, laser, light emitting chemical species capable of exciting or changing the reporting species;

(e) When the sequencing reaction is performed by passing the four individual dNTP molecules sequentially one at a time over the beads, and with sufficient and appropriate washing between additions, a proton is released from the PTP complex; the pH-sensing dye within the bead or upon a surface captures the released proton which changes the optical properties of the dye;

(f) When excited at a proper and suitable wavelength, and with proper excitation and emission filters present, the beads therefore emit light in proportion to the type and number of nucleotides incorporated into the extending primer as described above (the details of the sequencing chemical reactions are provided in an example below);

(g) The emitted light is collected through the optical emission filter, its intensity measured with the light detector;

(h) Light emitted from beads which lack an essential component of the sequencing reaction, such as no DNA or no polymerase, is measured and used as a negative control;

(i) The corrected emission is analyzed to determine which and how many of each of the four nucleotides were incorporated into the primer thereby allowing the sequence of the target strand to be determined; and (j) After determining as long a sequence as possible, the apparatus is washed free of beads and reagents and reused for sequencing the next batch of beads.

It is clear to those skilled in the art that if the high-pass dichroic mirror or interference filter were perfectly efficient, such that it could block all of the direct excitation radiation from the excitation source, then the low-pass dichroic mirror would not be needed.

In one embodiment, a magnet array is used to hold magnetic beads in an array to facilitate imaging. For example, an array of either permanent magnets or electromagnets, with the magnet size comparable to the diameter of a bead on which the sequencing reaction is taking place, which can be placed beneath the plane of the optical sensor (below as described in FIG. 5, i.e., on the side opposite the beads and sensor plane from the high pass filter) will cause the beads to localize such that each individual bead may be imaged. A single layer of beads is obtained by judiciously balancing the strength of each magnet pad, the magnetic strength of the beads and the flow rate of the solution passing over the sensor. When the beads have been imaged the array-forming magnets are removed or de-energized so that the imaged beads are released and a new batch of beads is localized onto the array for analysis.

Therefore, the optical sensing apparatus described in this section provides large improvements in cost, speed or reaction and ease of use compared to imaging the samples with a traditional microscope or other optical apparatus or measuring protons released with a pH sensitive electrode and employing unlabeled nucleotide reagents.

Example

The following illustrative example of using a system of the present invention to sequence a DNA molecule, should not be construed to limit the scope of the invention in any way as many variants of the following procedures will be obvious to those skilled in the art:

(A) A DNA sample (target), which may be prepared by many different methods, is readied for sequencing analysis by hybridizing the target to be sequenced to a capture probe/primer on the solid surface or bead surface and adding polymerase and other necessary reagents to give a PTP complex; only one DNA sequence, but many copies, is normally present on any given region or bead; alternatively, the DNA to be sequenced could be bound directly to the surface through covalent, electrostatic or hydrogen bonding interactions and the primer supplied to the solution;

(B) Nearby the PTP complex, and preferably bonded to the same solid surface or bead surface as the PTP complex, a pH-sensing dye molecule is attached such that the PTP complex and the dye are co-mingled on a molecular level and are less than one molecular diameter apart (about <1 nm); in order to ensure the complete capture of all released protons the ratio of dye to PTP is greater than zero and may be greater than one; this pH-sensing dye will readily combine with the protons released from the extending primer in the PTP complex with a concomitant change in its optical or physical properties;

(C) The beads or region on the surface of interest, with the DNA to be sequenced attached, are placed into an apparatus such as that shown in FIG. 5, or another apparatus which can adequately and equivalently measure the requisite changes in optical properties associated with the proton release;

(D) The beads or surfaces are configured into an apparatus capable of holding a solution of the dNTP, polymerase, washing buffers and other solution reagents; the beads or surfaces are preferably configured into a flow system so that various reagents (e.g., dNTP solutions) and washing solutions can be flowed over the static beads or surfaces;

(E) The beads are treated with an appropriate solution to reset the optical properties to the unprotonated state which is capable of detecting a change in pH from proton release. In the case of the pHrodo dye described earlier a solution of pH=10 changes the dye back to its colorless, non-fluorescent state ready for the next dNTP addition;

(F) Solutions of the four individual dNTP molecules are each separately passed over the beads or surface containing the PTP complex with appropriate washing to remove the previous dNTP between each addition;

(G) When the correct dNTP is added, i.e., a dNTP complementary to the base to be determined in the target strand (FIG. 2B), it is incorporated into the extending primer and protons (among other species) are released;

(H) The proton is captured by the surrounding pH-sensing agent;

(I) The pH-sensing agent entity changes its chemical, optical or physical properties upon reaction with the proton and the change may be correlated with the efficiency of the dNTP incorporation especially how many of a particular dNTP were incorporated; in this example the pH-sensing dye changes from a non-fluorescent state at higher pH values (pH=8-10) to a fluorescent state when protonated (FIG. 7);

(J) Using the apparatus depicted in FIG. 5, or an optical system which provides the same functionality (vide supra), the emission form the fluorescent beads are measured and the identity of the dNTP incorporated determined;

(K) Steps (E) through (J) are repeated and the order and identity of each dNTP incorporated are noted; and (L) Analysis of the data obtained relating change in pH-sensing agent with dNTP addition allows the determination of the sequence of the nucleotides in the target strand to be sequenced.

Embodiments of the Invention

A first embodiment of the invention includes a composition for sequencing nucleic acids including:
(g) a solid surface comprising a reactive group;
(h) a strand of nucleic acid
(i) a pH-sensing agent;
(j) a nucleic acid polymerase;
(k) at least one dNTP reagent; and
(l) a reaction solution.

A second embodiment includes the composition of the first embodiment, where the solid surface is selected from agarose, silica, organic polymers, glass, inorganic materials, phosphors, clay and combinations thereof.

A third embodiment includes the composition of the first embodiment, wherein the reactive group is selected from C—OH, —CO$_2$H, —NH$_2$, —SH, —CONH$_2$, —CO$_2$CH$_3$, epoxides R$_2$—C(O)C—R$_2$, C—X (where R=H or any alkyl or aryl group), alcohols, carboxylic acids, organic esters, amides, amines, alky or aryl halides, sulfates, phosphates, silanols, hydroxide or combinations thereof.

A fourth embodiment includes the composition of the third embodiment, where the reactive group is attached to a material selected from the group consisting of molecules, polymers, colloids, nanoparticles, and combinations thereof.

A fifth embodiment includes the composition of the first embodiment, where the pH-sensing agent is a pH-sensitive dye.

A sixth embodiment includes the composition of the sixth embodiment, where the pH-sensitive dye is non-fluorescent at basic pH and fluorescent at neutral or acidic pH.

A seventh embodiment includes the composition of the first embodiment, where the pH-sensing agent is selected from the group consisting of:

| INDICATOR NAME | pH, | COLOR |
| --- | --- | --- |
| Malachite green oxalate | 2.0, | green-blue |
| Brilliant green | 2.6, | green |
| Eosin yellowish | 3.0, | green fluoresc. |
| Erythrosine B | 3.6, | red |
| Methyl green | 2.3, | blue |
| Methyl violet | 2.7, | violet |
| Picric acid | 1.0, | yellow |
| Cresol red | 1.8, | yellow |
| Crystal violet | 2.6, | blue/violet |
| m-Cresol purple | 2.8, | yellow |
| Thymol blue | 2.8, | yellow |
| p-Xylenol blue | 2.8, | yellow |
| Eosin, bluish | 2.4, | pink fluoresc. |
| Quinaldine red | 3.2, | pink |
| 2,4-Dinitro phenol | 4.7, | yellow |
| 4-(Dimethylamino) azo | 4.0, | yellow/orange |
| Bromochlorophenol blue | 4.6, | blue/violet |
| Bromophenol blue | 4.6, | blue/violet |
| Congo red | 5.2, | yellow/orange |
| Methyl orange | 4.4, | yellow/orange |
| Bromocresol green | 5.4, | blue |
| 2,5-Dinitrophenol | 5.8, | yellow |
| Alizarin sulphonic acid | 6.3, | violet |
| Methyl red | 6.2, | yellow/orange |
| Chlorophenol red | 6.4, | purple |
| Litmus | 8.0, | blue |
| Bromocresol purple | 6.8, | purple |
| Bromophenol red | 6.8, | purple |
| 4-Nitrophenol | 7.5, | yellow |

-continued

| INDICATOR NAME | pH, | COLOR |
|---|---|---|
| Bromoxylenol blue | 7.5, | blue |
| Bromothymol blue | 7.6, | blue |
| Phenol red | 8.2, | red/violet |
| 3-Nitrophenol | 8.6, | yellow/orange |
| Neutral red | 8.0, | orange/yellow |
| Creosol red | 8.8, | purple |
| 1-Naphtholphthalein | 8.3, | blue/green |
| m-Cresol purple | 9.0, | purple |
| Thymol blue | 9.6, | blue |
| p-Xylenol blue | 9.6, | blue |
| Phenolphthalein | 9.8, | red/violet |
| Thymolphthalein | 10.5, | blue |
| Alkali blue | 14.0, | pink |
| Alizarin yellow GG | 12.1, | brown/yellow |
| Indigo carmine | 13.0, | yellow |
| Epsilon blue | 13.0, | violet |
| Titan yellow | 13.0, | red |

An eight embodiment includes the composition of the first embodiment, where the strand of nucleic acid is bound to said surface via a bond selected from covalent bond, electrostatic bond, hydrogen bond or combinations thereof.

A ninth embodiment includes the composition of the first embodiment, where the dye molecule is bound to the surface via a bond selected from covalent bond, electrostatic bond, hydrogen bond or combinations thereof.

A tenth embodiment includes the composition of the fifth embodiment, where the dye molecule is adjacent to the bound nucleic acid.

An eleventh embodiment includes the composition the first embodiment, where components in the reaction solution include a PCR mix.

A twelfth embodiment includes a method for sequencing DNA including the steps of:
(A) Providing a pH-sensing agent and a reactive surface;
(B) Attaching the pH-sensing agent to the reactive surface;
(C) Providing a nucleic acid priming sequence;
(D) Attaching the nucleic acid priming sequence to the reactive surface;
(E) Providing a nucleic acid to be sequenced;
(F) Providing a polymerase enzyme and a reaction solution;
(G) Adding the polymerase enzyme, the reaction solution, and the nucleic acid to be sequenced to the surface containing the pH-sensitive agent and the surface-bound primer;
(H) Resetting the pH-sensing agent by washing with a high pH solution;
(I) Providing individual solutions of four dNTP reagents selected from: dATP, dGTP, dCTP, dTTP and combinations thereof;
(J) Adding the four dNTP reagents individually and sequentially washing with the high pH solution between each addition;
(K) Measuring a change in the properties of the pH-sensing agent after each addition of each dNTP;
(L) Correlating the change in the properties of the pH-sensing agent with the type and amount of each dNTP added;
(M) Using the change in properties to determine a nature and an amount of dNTP incorporated at each step;
(N) Determining the nucleotide sequence from the dNTP incorporation data; and
(O) Repeating steps (h) through (l) until the order of nucleotides in the nucleic acid strand is determined.

A thirteenth embodiment includes the twelfth embodiment, where the nucleic acid is DNA.

A fourteenth embodiment includes the twelfth embodiment, where the change in the properties of the pH-sensitive agent are compared to a second control sample that does not include said polymerase enzyme.

A fifteenth embodiment includes the twelfth embodiment, where the nucleic acids and pH-sensitive agent are attached to said surface by covalent, electrostatic or hydrogen bonding interactions.

A sixteenth embodiment includes the twelfth embodiment, where the nucleic acid primer is attached to the surface by hybridizing it to a previously immobilized complementary DNA strand previously bound to the surface.

A seventeenth embodiment includes the twelfth embodiment, where the nucleic acid sequence to be sequenced is attached to the surface by hybridizing it to a complementary DNA strand previously bound to the surface.

An eighteenth embodiment includes the twelfth embodiment, where the nucleic acid to be sequenced is attached to said surface.

A nineteenth embodiment includes the twelfth embodiment, where the pH-sensing agent is not covalently bound to said surface but is in solution adjacent to the nucleic acid being sequenced A twentieth embodiment includes an apparatus for determining a DNA sequence including:
a. light-sensitive detector covered with a high-pass interference filter or dichroic mirror;
b. a surface, wherein the surface is adjacent to the light-sensitive detector and the interference filter or dichroic mirror is between the surface and the light-sensitive detector
c. an opening to introducing beads onto the surface adjacent to the detector
d. a bead dispenser or applicator to introduce beads onto the surface
e. a dispensing device to deliver reagents to the beads which contain the nucleic acid to be sequenced and to provide washing and conditioning fluids
f. an excitation source which measures the change in properties of the pH-sensitive agent
g. a low-pass excitation filter or dichroic mirror, wherein the low-pass excitation filter or dichroic mirror is located between the sample and the excitation source;
h. a means of correlating the emitted light with the amount and type of each dNTP added A twenty-first embodiment includes the twentieth embodiment, where there is no low pass dichroic mirror or filter.

A twenty-second embodiment includes the twentieth embodiment, where a syringe pump or other fluid moving device provides the means to load, wash and react the samples with fluids.

A twenty-third embodiment includes the twentieth embodiment, where the excitation source is an LED, laser, incandescent filament, laser diode or other light source.

A twenty-fourth embodiment includes the twentieth embodiment, where the light-sensitive detector is a CMOS photodiode or other light sensing CMOS circuit, a CCD, an imaging plate or light sensitive film.

A twenty-first embodiment includes the twentieth embodiment, further including a fiber optic face plate, wherein said fiber optic face plate is between the beads and said light-sensitive detector.

Summary

Techniques, methods, apparatus, reagents and materials which together form a system of the present invention can be used to sequence the order of the nucleotides in a molecule of DNA. These improvements will provide a less expensive, more accurate and faster means to sequence DNA molecules.

I claim:
1. A composition for sequencing nucleic acids comprising:
(a) a solid surface comprising a reactive group;
(b) a strand of nucleic acid;
(c) a pH-sensing agent;
(d) a nucleic acid polymerase;
(e) at least one dNTP reagent; and
(f) a reaction solution;
wherein said pH-sensing agent comprises a pH-sensitive dye, the pH-sensitive dye being non-fluorescent at basic pH and fluorescent at neutral or acidic pH.

2. A composition of claim 1, wherein said solid surface is selected from the group consisting of agarose, silica, organic polymers, glass, inorganic materials, phosphors, clay and combinations thereof.

3. A composition of claim 1, wherein said reactive group is selected from the group consisting of C—OH, —CO$_2$H, —NH$_2$, —SH, —CONH$_2$, —CO$_2$CH$_3$, epoxides, alcohols, carboxylic acids, organic esters, amides, amines, alky or aryl halides, sulfates, phosphates, silanols, hydroxide or combinations thereof.

4. A composition of claim 3, wherein said reactive group is attached to a material selected from the group consisting of molecules, polymers, colloids, nanoparticles, and combinations thereof.

5. A composition of claim 1, wherein said strand of nucleic acid is bound to said surface via a bond selected from the group consisting of covalent bond, electrostatic bond, hydrogen bond or combinations thereof.

6. A composition of claim 1, wherein the components in said reaction solution comprises a PCR mix.

7. A composition for sequencing nucleic acids comprising:
(a) a solid surface comprising a reactive group;
(b) a strand of nucleic acid;
(c) a pH-sensing agent;
(d) a nucleic acid polymerase;
(e) at least one dNTP reagent; and
(f) a reaction solution;
wherein said pH-sensing agent is bound to said surface via a bond selected from the group consisting of covalent bond, electrostatic bond, hydrogen bond or combinations thereof.

8. A composition for sequencing nucleic acids comprising:
(a) a solid surface comprising a reactive group;
(b) a strand of nucleic acid;
(c) a pH-sensing dye;
(d) a nucleic acid polymerase;
(e) at least one dNTP reagent; and
(f) a reaction solution;
wherein said strand of nucleic acid comprises a nucleic acid bound to the solid surface and wherein said pH-sensing dye is adjacent to said nucleic acid bound to the solid surface.

9. A method for sequencing DNA comprising the steps of:
(a) providing a pH-sensing agent and a reactive surface;
(b) providing a nucleic acid priming sequence;
(c) attaching said nucleic acid priming sequence to said reactive surface;
(d) providing a nucleic acid to be sequenced;
(e) providing a polymerase enzyme and a reaction solution;
(f) adding said polymerase enzyme, said reaction solution, and said nucleic acid to be sequenced to the surface containing said pH-sensitive agent and said surface-bound primer;
(g) resetting said pH-sensing agent by washing with a pH resetting solution, which resets the pH-sensing agent;
(h) providing individual solutions of four dNTP reagents selected from the group consisting of: dATP, dGTP, dCTP, and dTTP;
(i) adding said individual solutions of four dNTP reagents individually and sequentially washing with said pH resetting solution between each addition;
(j) measuring a change in the properties of the pH-sensing agent after each addition of each dNTP;
(k) correlating said change in the properties of the pH-sensing agent with the type and amount of each dNTP added;
(l) using said change in properties to determine a nature and an amount of dNTP incorporated at each step;
(m) determining the nucleotide sequence from the dNTP incorporation data; and
(n) repeating steps (g) through (k) until the order of nucleotides in the nucleic acid strand is determined.

10. The method of claim 9, wherein said nucleic acid to be sequenced is DNA.

11. The method of claim 9, wherein said change in the properties of the pH-sensitive agent are compared to a second control sample that does not include said polymerase enzyme.

12. The method of claim 9, wherein the nucleic acid to be sequenced and pH-sensitive agent are attached to said surface by covalent, electrostatic or hydrogen bonding interactions.

13. The method of claim 9, wherein said nucleic acid primer is attached to the surface by hybridizing it to a previously immobilized complementary DNA strand previously bound to the surface.

14. The method of claim 9, wherein said nucleic acid to be sequenced is attached to the surface by hybridizing it to a complementary DNA strand previously bound to the surface.

15. The method of claim 9, wherein the nucleic acid to be sequenced is attached to said surface.

16. The method of claim 9, wherein the pH-sensing agent is covalently bound to said surface.

17. The method of claim 9, wherein the pH-sensing agent is in solution adjacent to the nucleic acid to being be sequenced.

18. A composition for sequencing nucleic acids comprising:
(a) a solid surface comprising a reactive group;
(b) a strand of nucleic acid;
(c) a pH-sensing agent;
(d) a nucleic acid polymerase;
(e) at least one dNTP reagent; and
(f) a reaction solution;
wherein said pH-sensing agent is selected from the group consisting of: Malachite green oxalate; Brilliant green; Eosin yellowish; Erythrosine B; Methyl green; Methyl violet; Picric acid; Cresol red; Crystal violet; m-Cresol purple; Thymol blue; p-Xylenol blue; Eosin, bluish; Quinaldine red; 2,4-Dinitro phenol; 4-(Dimethylamino) azo; Bromochlorophenol blue; Bromophenol blue; Congo red; Methyl orange; Bromocresol green; 2,5-Dinitrophenol; Alizarin sulphonic acid; Methyl red; Chlorophenol red; Litmus; Bromocresol purple; Bromophenol red; 4-Nitrophenol; Bromoxylenol blue; Bromothymol blue; Phenol red; 3-Nitrophenol; Neutral red; Creosol red; 1-Naphtholphthalein; m-Cresol purple; Thymol blue; p-Xylenol blue; Phenolphthalein; Thymolphthalein; Alkali blue; Alizarin yellow GG; Indigo carmine; Epsilon blue; and Titan yellow.

19. A method for sequencing DNA comprising the steps of:
(a) providing a pH-sensing agent and a reactive surface;

(b) providing a nucleic acid to be sequenced;
(c) attaching said nucleic acid to said reactive surface;
(d) providing a nucleic acid priming sequence;
(e) providing a polymerase enzyme and a reaction solution;
(f) adding said polymerase enzyme, said reaction solution, and said priming sequence to the surface containing said pH-sensitive agent and said surface-bound nucleic acid to be sequenced;
(g) resetting said pH-sensing agent by washing with a pH resetting solution, which resets the pH-sensing agent;
(h) providing individual solutions of four dNTP reagents selected from the group consisting of: dATP, dGTP, dCTP, and dTTP;
(i) adding said individual solutions of four dNTP reagents individually and sequentially washing with said pH resetting solution between each addition;
(j) measuring a change in the properties of the pH-sensing agent after each addition of each dNTP;
(k) correlating said change in the properties of the pH-sensing agent with the type and amount of each dNTP added;
(l) using said change in properties to determine a nature and an amount of dNTP incorporated at each step;
(m) determining the nucleotide sequence from the dNTP incorporation data; and
(n) repeating steps (g) through (k) until the order of nucleotides in the nucleic acid strand is determined.

* * * * *